United States Patent
Giera et al.

(10) Patent No.: US 6,316,673 B2
(45) Date of Patent: Nov. 13, 2001

(54) PROCESS FOR PRODUCING AMINODIPHENYLAMINES

(75) Inventors: Henry Giera, Grosskitzighofen (DE); Torsten Pohl, Cambridge, MA (US); Uwe Hugger, Rellingen (DE); Adolf Sicheneder, Hohenlockstedt (DE); Fred Schuhmacher, Schenefeld (DE); Adolf Brill, Brunsbüttel (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/776,104

(22) Filed: Feb. 2, 2001

(30) Foreign Application Priority Data

Feb. 9, 2000 (DE) .............................. 100 05 601

(51) Int. Cl.$^7$ ................................ C07C 209/00
(52) U.S. Cl. ..................... 564/423; 564/395; 564/406
(58) Field of Search .................... 564/423, 406, 564/395

(56) References Cited

U.S. PATENT DOCUMENTS

| | | | |
|---|---|---|---|
| 4,122,118 | 10/1978 | George et al. | 260/576 |
| 4,187,248 | 2/1980 | Merten et al. | 260/576 |
| 4,187,249 | 2/1980 | Maender et al. | 260/576 |
| 4,665,232 | 5/1987 | Podder et al. | 564/406 |
| 4,670,595 | 6/1987 | Podder et al. | 564/406 |
| 5,576,460 | 11/1996 | Buchwald et al. | 564/386 |
| 5,831,128 | 11/1998 | Beller et al. | 564/405 |
| 5,840,982 | 11/1998 | Reynolds et al. | 564/423 |
| 6,235,937 | 5/2001 | Giera et al. | 564/406 |

FOREIGN PATENT DOCUMENTS

| | | |
|---|---|---|
| 185683 | 6/1907 | (DE) . |
| 32 46 151 | 6/1984 | (DE) . |

OTHER PUBLICATIONS

Kirk–Othmer, Encyclopedia of Chemical Technology, 4$^{th}$ edition, vol. 3, (month unavailable) 1992, pp. 424–456, Antioxidants.

Ullmann's Encyclopedia of Industrial Chemistry, 5$^{th}$ edition, vol. A3, (month unavailable) 1985, pp. 91–111, Antioxidants.

Christian S. Rondestvedt Jr.: "Synthesis of 4–Aminodiphenylamine and Its Relatives", Journal of Organic Chemistry, Bd. 42, Nr. 10, 1977, Seiten 1786–1790, XP002166757, American Chemical Society, Easton., US ISSN: 0022–3263, Seite 1787, Splate 2, Zeile 33–Seite 1790, Spalte 2, Zeile 48.

Primary Examiner—Samuel Barts
(74) Attorney, Agent, or Firm—Joseph C. Gil; Noland J. Cheung

(57) ABSTRACT

The present invention relates to the production of aminodiphenyl-amines resulting in good yields and high purity levels when aromatic amines are reacted with nitrohalobenzenes in the presence of a palladium catalyst and a base and the product thus obtained is subsequently hydrogenated with hydrogen.

9 Claims, No Drawings

PROCESS FOR PRODUCING AMINODIPHENYLAMINES

FIELD OF THE INVENTION

The invention relates to a process for producing aminodiphenyl-amines, particularly 4-aminodiphenylamine (4-ADPA), by reacting nitrohalobenzenes with aromatic amines in the presence of a palladium catalyst and a base and subsequently hydrogenating the intermediate product thus obtained.

BACKGROUND OF THE INVENTION 4-aminodiphenylamine (4-ADPA) is an important starting product for the synthesis of antioxidants and stabilizers in the rubber and polymer industry (Kirk-Othmer, Encyclopedia of Chemical Technology, $4^{th}$ Edition, 1992, Vol. 3, page 424–456; Ullmann's Encyclopedia of Industrial Chemistry, $5^{th}$ Edition, Vol. A3, 1985, pages 91–111).

4-ADPA may be produced by various methods. One possible method of producing 4-ADPA is the two-stage reaction of aniline or aniline derivatives with p-nitrochlorobenzene in the presence of an acid acceptor or a neutralizing agent, optionally in the presence of a catalyst. Production by this method is described, for example, in DE-A 3,246,151, DE-A 3,501,698, DE-A 185663, U.S. Pat. Nos. 4,670,595, 4,187,249 and 4,187,248. The first stage is generally performed using copper catalysts, and the second stage is performed with different metal components, e.g. nickel (see for example U.S. Pat. No. 5,840,982). Reactions also of, for example, halogenated nitrobenzenes with amines in the presence of palladium catalysts are described in U.S. Pat. No. 5,576,460 and EP-A 846,676.

The disadvantage of the processes described in the above literature is frequently inadequate selectivity, in particular, during formation of the intermediate product, whereby yield losses occur as a result of more or less complex purification steps, before the 4-aminodiphenylamines may be formed by hydrogenation.

SUMMARY OF THE INVENTION

It was, therefore, desirable to provide a process for producing aminodiphenylamines, which starts from aromatic amines and, through reaction with appropriate nitrohalobenzenes and subsequent hydrogenation of the intermediate product formed, results in the desired aminodiphenylamines having good yield and elevated purity.

Therefore, the present invention provides a process for producing aminodiphenylamines by reacting nitrohalobenzenes with aromatic amines in the presence of a base and palladium catalyst and subsequently hydrogenating the product obtained with hydrogen.

DETAILED DESCRIPTION OF THE INVENTION

The nitrohalobenzenes used are preferably those in which the nitro group is in para-position relative to the halogen residue. Possible halogen residues are: fluorine, chlorine, bromine and iodine, preferably chlorine and bromine. The nitrohalobenzenes may also be substituted by one or more other residues, such as for example $C_1$–$C_4$ alkyl residues. Naturally, the position of the nitro group relative to the halogen residues may also be other than the para-position, e.g. it may be in position 2 or 3.

Nitrohalobenzenes used in the present invention are: 4-nitro-2-methylchlorobenzene, 4-nitro-3-methylchlorobenzene, 4-nitrochloro-benzene, 3-nitrochlorobenzene and 2 nitrochlorobenzene. 4-nitrochloro-benzene is preferred.

Aromatic amines which may be used in the process according to the present invention are those aromatic amines which are known in relation to such a reaction, for example aniline, o-toluidine, m-toluidine, p-toluidine, 4-ethylaniline, 4-butylaniline, 4-isopropylaniline, 3,5-dimethyl-aniline or 2,4-dimethylaniline. Aniline is preferred. Naturally, the aromatic amines may also be used in the form of mixtures, in particular isomer mixtures.

In the process according to the invention, 1 to 10 mol, preferably 1.5 to 6 mol, and most preferably 2 to 4 mol of the aromatic amine, are generally used per mol of nitrohalobenzene.

According to the present invention, palladium catalysts, e.g. palladium/phosphine complexes, or other known palladium compounds or complexes may be used.

Suitable palladium/phosphine complex compounds are those in which the palladium has the valency 0 or II and suitable phosphine ligands are compounds such as triphenylphosphine, tri-o-toluylphosphine, tricyclohexylphosphine, tri-t-butylphosphine, bisdiphenylphosphine ethane, bisdiphenylphosphine propane, bis (diphenylphosphino)butane, bis(dicyclohexylphosphino) ethane, bis(diphenylphosphino)ferrocene, 5,5'-dichloro-6,6'-dimethoxybiphenyl-2,2'-diyl-bisdiphenylphosphine, bis-4, 4'-dibenzofuran-3,3'-yl-bisdiphenylphosphine, 1,1'-bis (diphenylphosphino)diphenyl ether or bis (diphenylphosphino)binaphthyl, wherein the stated phenyl residues may be substituted by sulfonic acid residues and/or by one or more $C_1$–$C_{12}$ alkyl groups or $C_3$–$C_{10}$ cycloalkyl groups. In addition, polymer-bound phosphines may serve as ligands, e.g. tPP polymer (commercially available). Triphenylphosphine is preferably used as a ligand.

However, other palladium/phosphine complex compounds may also be used for the process according to the present invention, such as for example, nitrogen- or oxygen-containing ligands, such as 1,10-phenanthroline, diphenylethane diamine, [1,1']-binaphthenyl-2,2'-diol (BINOL) and 1,1'-binaphthenyl-2,2'-dithiol (BINAS), or indeed those with two or more different heteroatoms, such as O, N, S.

Palladium compounds which may serve as catalysts include the following classes of compound, for example: palladium halides, acetates, carbonates, ketonates, nitrates, acetonates or palladacyclene, for example $Pd_2dba_3$, $Pd(acac)_2$, $Pd(OAc)_2$, $PdCl_2$, $(CH_3CN)_2Pd(NO_2)Cl$. $Pd_2dba_3$, $Pd(acac)_2$, $Pd(OAc)_2$, $PdCl_2$ are preferred. In addition, heterogeneous or immobilized palladium catalysts may also be used in the process according to the present invention, i.e. those which are applied to suitable inert supports, for example.

In the case of the palladium/phosphine complexes to be used according to the present invention, the molar ratio of the corresponding ligands to palladium is approximately 40:1 to 1:1, preferably 10:1 to 2:1, most preferably 8:1 to 4:1.

According to the present invention, the palladium catalysts, such as palladium/phosphine complexes and/or the other complexes or compounds which may be used, are generally used in amounts of from 0.0001 mol % to 10 mol %, preferably 0.001 mol % to 5 mol %, relative to the nitrohalobenzenes used.

Bases which may be used in the process according to the present invention are alkali and/or alkaline earth metal carbonates, alkoxides and/or hydroxides, in particular, potassium and/or sodium carbonate, cesium carbonate, sodium methanolate and barium hydroxide. Potassium and/or sodium carbonate are preferably used. The bases may be used in a substoichiometric amount or in an excess of up to ten times the equivalent amount relative to the nitrohalobenzene. The bases are preferably used in a 0.3 to 2 times equivalent amount, relative to nitrohalobenzene.

It is advantageous for the process according to the present invention for the bases used to be pretreated by grinding and/or drying.

In the process according to the invention, grinding may be performed in commercially available mills. Grinding affects a drastic increase in specific surface area, which results in a clear increase in conversion. In many cases, grinding may increase the specific surface area by a factor of 10 to 20.

After grinding, the specific areas of the bases are approx. 0.1 to 10 $m^2/g$, preferably 0.2 to 1 $m^2/g$ (BET).

As a result of the pronounced hygroscopic properties of the bases used in the process according to the present invention, the latter have a tendency towards the more or less marked absorption of atmospheric constituents, such as water or carbon dioxide. From a level of absorption of atmospheric constituents of approx. 30 weight percent, a marked influence on achievable conversion levels may be noted. Therefore, in addition to grinding, drying of the bases is also frequently indicated.

Drying of the bases proceeds, for example, in that they are heated under a reduced pressure of approx. 0.01 to 100 mbar for several hours to temperatures of approx. 50 to 200° C., preferably 100 to 160° C.

The first stage of the process according to the present invention may be performed at temperatures in the range of from 20 to 250° C., preferably at temperatures of from 120 to 180° C. The reaction temperatures depend, in particular, on the type of starting products, the catalyst and the bases used.

The process according to the present invention may be performed both in the presence and in the absence of a suitable solvent. Examples of possible solvents are inert organic hydrocarbons, such as xylene and toluene. In addition, the aromatic amines used may themselves function as solvents.

In the process according to the present invention, the reaction water arising may, if desired (as in DE-A 26 33 811 and DE-A 32 46 151), be removed, for example, by distillation with the aid of a suitable entraining agent.

The amount of solvent used may be readily determined by appropriate preliminary tests.

The process according to the present invention may be performed continuously or discontinuously by conventional methods.

In the process according to the present invention, the reaction product obtained after reaction of the aromatic amines with the halonitroaromatics is hydrogenated with hydrogen, wherein hydrogenation may be performed in the presence of the palladium catalyst already present, optionally with the addition of a suitable inert catalyst support.

It is also possible to perform hydrogenation in the presence of additional hydrogenation catalysts, such as those on a nickel, palladium or platinum basis, optionally using a suitable catalyst support.

Suitable materials for use as catalyst support are all industrially conventional catalyst supports based on carbon, elemental oxides, elemental carbides or elemental salts in various forms. Examples of carbon-containing supports are coke, graphite, carbon black or activated carbons. Examples of elemental oxide catalyst supports are $SiO_2$ (natural or synthetic silicic acid, quartz), $Al_2O_3$ ($\alpha$-, $\gamma$-$Al_2O_3$), aluminas, natural or synthetic aluminosilicates (zeolites), phyllosilicates such as bentonite and montmorillonite, $TiO_2$ (rutile, anatase), $ZrO_2$, MgO or ZnO. Examples of elemental carbides and salts are SiC, $AlPO_4$, $BaSo_4$, $CaCO_3$. In principle, both synthetic materials and supports from natural sources, such as pumice stone, kaolin, bleaching earths, bauxites, bentonites, diatomaceous earth, asbestos or zeolites, may be used.

Further supports which may be used for the catalysts usable according to the present invention are elemental mixed oxides and hydrogenated oxides of elements of the groups 2 to 16 of the periodic table together with rare-earth metals (atomic numbers 58 to 71), preferably from the elements Al, Si, Ti, Zr, Zn, Mg, Ca, Sn, Nb and Ce, which may inter alia be produced by means of mechanical mixing, joint precipitation of salts or via cogels of salts and/or alkoxides, as known to the person skilled in the art.

The supports may be used both as chemically uniform pure substances and as mixtures. Materials in both lump and powder form are suited for use according to the present invention as catalyst supports. Where the supported catalyst is arranged as a fixed bed, the support is preferably used in the form of molded articles, e.g. balls, cylinders, rods, hollow cylinders or rings. Catalyst supports may optionally be further modified by extrusion, tabletting, optionally with the admixture of further catalyst supports or binders, such as $SiO_2$ or $Al_2O_3$, and calcining. The inner surface area of the support (BET surface area) is 1 to 2000 $m^2/g$, preferably 10 to 1600 $m^2/g$, most preferably 20 to 1500 $m^2/g$. Preparation and further processing are well known to the person skilled in the art and are known in the prior art.

Activated carbons and Si-, Al-, Mg-, Zr- and Ti-containing materials are preferably used as support materials. Activated carbon is most preferred.

The above-mentioned supports may also be loaded with palladium with a metal content of from 0.01 to 50 wt. %, preferably 0.1 to 10 wt. %, relative to the total weight of the catalyst.

The above-mentioned support materials or the support materials loaded with palladium may be used in amounts of from 0.01 to 20 wt. %, relative to the halonitrobenzene used, preferably in amounts of from 0.01 to 10 wt. %. The use of activated carbon loaded with palladium is preferred.

Hydrogenation may also be performed using other reduction methods, as are known to the person skilled in the art and listed, for example, in "Reductions in Organic Chemistry, Second Edition, ACS Monograph 188".

The hydrogenation temperatures range from to approx. 0 to 200° C., particularly 40 to 150° C.; the pressures (hydrogen pressure) are around 0.1 to 150 bar, particularly 0.5 to 70 bar, most preferably 1 to 50 bar.

Using the process according to the present invention, corresponding 4-aminodiphenylamines are obtained with high selectivities (>98%) and in yields of up to 99%.

EXAMPLES

Example 1

372.0 g (4.00 mol) of aniline, 0.25 g (0.00082 mol) of palladium acetonylacetonate and 0.86 g (0.00328 mol) of triphenylphosphine are initially introduced into a multinecked, round-bottomed flask in an inert atmosphere and stirred for 10 minutes at room temperature. 157.6 g (1.00 mol) of 4-chloronitrobenzene are added and stirring is performed for a further 10 minutes at room temperature. Then, 120.0 g (0.87 mol) of ground potassium carbonate and 40 ml of xylene are added. Refluxing with water separation is performed with vigorous stirring for 45 mins. Gas-chromatographic monitoring shows complete conversion of para-chloronitrobenzene.

The mixture is allowed to cool to 85° C. and diluted with 300 ml of water. The organic phase is hydrogenated with 1.0 g Pd/C (5% Pd/C) for 15 mins at 10 bar of hydrogen pressure, wherein the temperature reaches 110° C.

After filtration and distillation, 182 g (99% of theoretical) of 4-aminodiphenylamine are obtained.

Example 2

372.0 g (4.00 mol) of aniline, 0.20 g (0.00066 mol) of palladium acetonylacetonate and 0.69 g (0.00263 mol) of triphenylphosphine are initially introduced into a multi-necked, round-bottomed flask in an inert atmosphere and stirred for 10 minutes at room temperature. 157.6 g (1.00 mol) of 4-chloronitrobenzene are added and stirring is performed for a further 10 minutes at room temperature. Then, 120.0 g (0.87 mol) of ground potassium carbonate and 40 ml of xylene are added. Refluxing with water separation is performed with vigorous stirring for 45 mins. Gas-chromatographic monitoring shows complete conversion of para-chloronitrobenzene.

The mixture is allowed to cool to 85° C. and diluted with 300 ml of water. The organic phase is hydrogenated with 1.0 g Pd/C (3% Pd/C) for 11 mins at 10 bar of hydrogen pressure, wherein the temperature reaches 120° C.

After filtration and distillation, 181 g (98% of theoretical) of 4-aminodiphenylamine are obtained.

Example 3

372.0 g (4.00 mol) of aniline, 0.25 g (0.00082 mol) of palladium acetonylacetonate and 0.86 g (0.00328 mol) of triphenylphosphine are initially introduced into a multi-necked, round-bottomed flask in an inert atmosphere and stirred for 10 minutes at room temperature. 157.6 g (1.00 mol) of 4-chloronitrobenzene are added and stirring is performed for a further 10 minutes at room temperature. Then, 96.6 g (0.70 mol) of ground potassium carbonate and 50 ml of xylene are added. Refluxing with water separation is performed with vigorous stirring for 45 mins. Gas-chromatographic monitoring shows complete conversion of para-chloronitrobenzene.

The mixture is allowed to cool to 85° C. and diluted with 300 ml of water. The organic phase is hydrogenated with 1.0 g Pd/C (5% Pd/C loading) for 14 mins at 10 bar of hydrogen pressure, wherein the temperature reaches 120° C.

After gas-chromatographic investigation, 99% of 4-aminodiphenyl-amine is obtained.

Example 4

372.0 g (4.00 mol) of aniline, 0.22 g (0.00098 mol) of palladium acetate and 1.04 g (0.00397 mol) of triphenylphosphine are initially introduced into a multi-necked, round-bottomed flask in an inert atmosphere and stirred for 10 minutes at room temperature. 157.6 g (1.00 mol) of 4-chloronitrobenzene are added and stirring is performed for a further 10 minutes at room temperature. Then, 96.6 g (0.70 mol) of ground potassium carbonate and 50 ml of xylene are added. Refluxing with water separation is performed with vigorous stirring for 45 mins. Gas-chromatographic monitoring shows complete conversion of para-chloronitrobenzene.

The organic phase is hydrogenated for 25 mins at 10 bar of hydrogen pressure, wherein the temperature reaches 140° C. After gas-chromatographic investigation, 98% of 4-aminodiphenylamine is obtained.

Example 5

372.0 g (4.00 mol) of aniline, 0.30 g (0.00098 mol) of palladium acetonylacetonate and 1.04 g (0.00397 mol) of triphenylphosphine are initially introduced into a multi-necked, round-bottomed flask in an inert atmosphere and stirred for 10 minutes at room temperature. 157.6 g (1.00 mol) of 4-chloronitrobenzene are added and stirring is performed for a further 10 minutes at room temperature. Then, 96.6 g (0.70 mol) of ground potassium carbonate and 50 ml of xylene are added. Refluxing with water separation is performed with vigorous stirring for 45 mins. Gas-chromatographic monitoring shows complete conversion of para-chloronitrobenzene.

The mixture is allowed to cool to 85° C. and diluted with 300 ml of water. The organic phase is hydrogenated for 34 mins at 10 bar of hydrogen pressure, wherein the temperature reaches 140° C.

After gas-chromatographic investigation, 99% of 4-aminodiphenylamine is obtained.

Example 6

372.0 g (4.00 mol) of aniline, 0.30 g (0.00098 mol) of palladium acetonylacetonate and 1.04 g (0.00397 mol) of triphenylphosphine are initially introduced into a multi-necked, round-bottomed flask in an inert atmosphere and stirred for 10 minutes at room temperature. 157.6 g (1.00 mol) of 4-chloronitrobenzene are added and stirring is performed for a further 10 minutes at room temperature. Then, 96.6 g (0.70 mol) of ground potassium carbonate and 50 ml of xylene are added. Refluxing with water separation is performed with vigorous stirring for 45 mins. Gas-chromatographic monitoring shows complete conversion of para-chloronitrobenzene.

The mixture is allowed to cool to 85° C. and diluted with 300 ml of water. The organic phase is hydrogenated after the addition of 2.0 g activated carbon for 24 mins at 10 bar of hydrogen pressure, wherein the temperature reaches 140° C.

After gas-chromatographic investigation, 99% of 4-ADPA is obtained.

Example 7

Pretreatment of Bases:

Commercially available potassium carbonate is ground, for example, for approx. 5 minutes in a kitchen or ball mill. The potassium carbonate made by Grüssing and treated in this way thereby experiences an increase in specific surface area from 0.04 m$^2$/g to 0.52 m$^2$/g and exhibits a primary crystallite size of 10 μm or less. The ground potassium carbonate is then dried for 5 hours at a pressure of 1 mbar and a temperature of 150° C. If other bases are used, these are pretreated in a similar manner.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing aminodiphenylamines comprising the steps of reacting aromatic amines with nitrohalobenzenes in the presence of a palladium catalyst and a base to produce a product and hydrogenating said product with hydrogen.

2. A process according to claim 1, wherein the nitro group of said nitrohalobenzene is in para-position relative to the halogen residue.

3. A process according to claim 1, wherein the aromatic amines are selected from the group consisting of aniline, o-toluidine, m-toluidine, p-toluidine, 4-ethylaniline, 4-butylaniline, 4-isopropylaniline, 3,5-dimethylaniline and 2,4-dimethylaniline.

4. A process according to claim 1, wherein 1 to 10 mol of aromatic amine is used per mol of nitrohalobenzene.

5. A process according to claim 1, wherein the palladium catalyst is a palladium/phosphine complex.

6. A process according to claim 5, wherein the molar ratio of phosphine to palladium is 40:1 to 1:1 in the palladium/phosphine complex.

7. A process according to claim 1, wherein the palladium catalysts are used in amounts of from 0.0001 mol % to 10 mol % relative to the nitrohalobenzenes used.

8. A process according to claim 1, wherein the bases used are pretreated by grinding and/or drying.

9. A process according to claim 1, wherein the specific surface areas of the bases after grinding ranges from 0.1 to 10 $m^2$/g (BET).

* * * * *